United States Patent [19]
Manning et al.

[11] Patent Number: 5,552,137
[45] Date of Patent: Sep. 3, 1996

[54] BIODEGRADABLE QUATERNARY HAIR CONDITIONERS

[75] Inventors: Monna M. Manning; Andrea S. Allardice, both of Columbus; Floyd Friedli, Dublin, all of Ohio

[73] Assignee: Witco Corporation, Greenwich, Conn.

[21] Appl. No.: 286,544

[22] Filed: Aug. 5, 1994

[51] Int. Cl.⁶ .................................................. A61K 7/75
[52] U.S. Cl. ........................... 424/70.1; 514/755; 514/873
[58] Field of Search ............................................ 424/70.1

[56] References Cited

U.S. PATENT DOCUMENTS

| | | | |
|---|---|---|---|
| 4,137,180 | 1/1979 | Naik et al. | 252/309 |
| 4,456,554 | 6/1984 | Walz et al. | 252/309 |
| 4,767,547 | 8/1988 | Straathof et al. | 252/309 |
| 4,808,321 | 2/1989 | Walley | 252/309 |
| 4,978,526 | 12/1990 | Gesslein et al. | 424/70 |

FOREIGN PATENT DOCUMENTS

| | | | |
|---|---|---|---|
| 1312619 | 1/1993 | Canada . | |
| 0309052 | 3/1989 | European Pat. Off. . | |
| 0409502 | 1/1991 | European Pat. Off. | 252/309 |
| 0409504 | 1/1991 | European Pat. Off. | 252/309 |
| 0443313 | 8/1991 | European Pat. Off. | 252/309 |
| 3402146 | 7/1985 | Germany | 252/309 |
| 1567947 | 5/1980 | United Kingdom . | |
| WO91/17975 | 11/1991 | WIPO . | |

OTHER PUBLICATIONS

Ash, 1977, A Formulary of Cosmetic Preparations, pp. 119–129.
Higashi et al. (1986) Surface Structure and Oxygen Permeation in Mixed Multi–bilayer Films of Hydrocarbon and Fluorocarbon Amphiphiles, *Macromolecules* 19:1362–1366.
Moss et al. (1990) Relation in Surfactant Monomer Stryucture to Flip–Flop Dynamics in Surface–Differentiated Synthetic Bilayer Membranes, *J. Am. Chem. Soc.* 112:6391–6392.
Kunitake et al. (1983) Excimer Formation and Phase Separation of Hydrocarbon and Fluorocarbon Bilayer Membranes *Bull Chem. Soc. Jpn.* 56:3235–3244.

*Primary Examiner*—Shelley A. Dodson
*Attorney, Agent, or Firm*—Scully, Scott, Murphy & Presser

[57] ABSTRACT

Disclosed are conditioning compositions for the hair and skin containing compounds of the formula $(R^1)(R^2)N(CHCH_2OC(O)R)_2X^-$ wherein $R^1$ is alkyl containing 1 to 6 carbon atoms, or hydroxyalkyl containing 1 to 6 carbon atoms; $R^2$ is alkyl containing 1 to 6 carbon atoms, or benzyl; $X^-$ is an anion; and R is alkyl and alkylene of 12 to 22 carbon atoms having 0 to 3 carbon-carbon double bonds, provided that at least 2 different chain lengths R are present and 0, 1 and 2 such double bonds are present.

14 Claims, No Drawings

BIODEGRADABLE QUATERNARY HAIR CONDITIONERS

BACKGROUND OF THE INVENTION

The present invention relates to conditioning hair and skin, particularly the hair and skin of the human body. More particularly, the present invention relates to methods of imparting conditioning to the hair and skin and to compositions useful as hair conditioners and skin conditioners.

Hair conditioning imparts to the hair many attributes which are perceivable and are considered to be desirable. That is, hair conditioners are used so that the hair feels, to the touch, smoother and softer. In addition, hair conditioners are used to render the hair more easily rinsable when it is washed or rinsed, to improve the wet and dry combability of the hair, and to impart to the hair greater ease of detangling and greater manageability to combing, brushing and styling.

Skin conditioners are used generally to improve the feel of the skin to the touch, rendering the skin softer and smoother feeling. In addition, skin conditioners are used to impart to the skin a feeling of fullness and smoothness as well as freedom from dryness and freedom from roughness.

Numerous compositions have been available commercially for conditioning the hair and the skin. More recently, however, governmental regulations and the preferences of the individual consumer have given rise to concerns that consumer products including hair conditioners and skin conditioners not pose excessive risks of damage to the environment. While these concerns have generally been addressed by improvements in composition so that materials when discarded or washed away are relatively less damaging to the environment, it would be useful to be able to formulate hair conditioning products and skin conditioning products which are in fact biodegradable. In this way, the desirable conditioning properties would be provided, and the product upon disposal or removal by washing and the like would be capable of biodegrading, that is, being converted by the processes normally encountered in waste water treatment and the like into components which pose an even lesser risk of harm to the environment and which can be dealt with ever more easily by the customary processes for treating solid waste and waste water.

Unfortunately, actual experience prior to the present invention has generally found that agents that might be considered in hair conditioning compositions and skin conditioning compositions, which agents are found to be biodegradable, perform only poorly if at all as conditioning agents for the hair and skin. In fact, this experience has been encountered so uniformly that there has seemed to be essentially a negative correlation between biodegradability and effectiveness as a conditioner for the hair and skin; that is, an agent found to be biodegradable would accordingly not be expected to, and would not, perform adequately as a conditioning agent for the hair and skin.

Thus, there remains a need for conditioning agents and for compositions containing such agents exhibiting biodegradability and also exhibiting exemplary performance as conditioners for the hair and skin. The present invention satisfies this need, even in the face of expectations to the contrary as drawn from experience with many biodegradable compounds.

BRIEF SUMMARY OF THE INVENTION

One aspect of the present invention is a method for conditioning hair comprising applying to the hair a conditioning effective amount of a composition comprising (a) from 0.1 wt. % to 10 wt. % of a mixture of compounds of the formula (1)

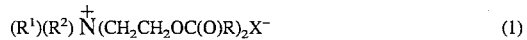  (1)

wherein $R^1$ is alkyl containing 1 to 6 carbon atoms, or hydroxyalkyl containing 1 to 6 carbon atoms; $R^2$ is alkyl containing 1 to 6 carbon atoms, or benzyl; $X^-$ is an anion; and R is selected from the group consisting of alkyl and alkylene groups containing 11 to 23 carbon atoms and up to 3 carbon-carbon double bonds, provided that said mixture contains compounds of formula (1) containing R groups which have at least 2 different chain lengths and containing R groups which have 0, 1 and 2 carbon-carbon double bonds; and (b) a vehicle which imparts to said composition fluidity upon application thereof to the hair and which has a pH value compatible with said hair.

Another aspect of the present invention is a method for conditioning skin comprising applying to the skin a conditioning effective amount of a composition comprising (a) from 0.1 wt. % to 10 wt. % of a mixture of compounds of the formula (1)

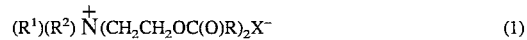  (1)

wherein $R^1$ is alkyl containing 1 to 6 carbon atoms, or hydroxyalkyl containing 1 to 6 carbon atoms; $R^2$ is alkyl containing 1 to 6 carbon atoms, or benzyl; $X^-$ is an anion; and R is selected from the group consisting of alkyl and alkylene groups containing 11 to 23 carbon atoms and up to 3 carbon-carbon double bonds, provided that said mixture contains compounds of formula (1) containing R groups which have at least 2 different chain lengths and containing R groups which have 0, 1 and 2 carbon-carbon double bonds; and (b) a vehicle which imparts to said composition fluidity upon application thereof to the skin and which has a pH value compatible with said skin.

Another aspect of the present invention is compositions useful for conditioning hair, comprising a) from 0.1 wt. % to 10 wt. % of a mixture of compounds of the formula (1)

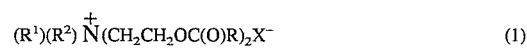  (1)

wherein $R^1$ is alkyl containing 1 to 6 carbon atoms, or hydroxyalkyl containing 1 to 6 carbon atoms; $R^2$ is alkyl containing 1 to 6 carbon atoms, or benzyl; $X^-$ is an anion; and R is selected from the group consisting of alkyl and alkylene groups containing 11 to 23 carbon atoms and up to 3 carbon-carbon double bonds, provided that said mixture contains compounds of formula (1) containing R groups which have at least 2 different chain lengths and containing R groups which have 0, 1 and 2 carbon-carbon double bonds; and (b) a vehicle which imparts to said composition fluidity upon application thereof to the hair and which has a pH value compatible with said hair.

Yet another aspect of the present invention is compositions useful for conditioning skin, comprising (a) from 0.1 wt. % to 10 wt. % of a mixture of compounds of the formula (1)

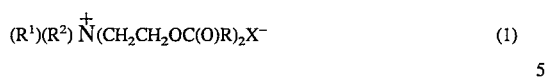

wherein $R^1$ is alkyl containing 1 to 6 carbon atoms, or hydroxyalkyl containing 1 to 6 carbon atoms; $R^2$ is alkyl containing 1 to 6 carbon atoms, or benzyl; $X^-$ is an anion; and R is selected from the group consisting of alkyl and alkylene groups containing 11 to 23 carbon atoms and up to 3 carbon-carbon double bonds, provided that said mixture contains compounds of formula (1) containing R groups which have at least 2 different chain lengths and containing R groups which have 0, 1 and 2 carbon-carbon double bonds; and (b) a vehicle which imparts to said composition fluidity upon application thereof to the skin and which has a pH value compatible with said skin.

DETAILED DESCRIPTION OF THE INVENTION

The compounds of formula (1) having any single chain length R and any given degree of saturation or unsaturation are known, individually, per se.

The desired mixture of compounds in accordance with this invention having compounds of several different chain lengths R and degrees of saturation and unsaturation can be synthesized by a series of reactions carried out under conditions familiar to those of ordinary skill in this art. For instance, a methyl-bis(2-hydroxyethyl) tertiary amine can be reacted with an appropriate blend of fatty acids of the general formula RC(O)OH as defined furthermore herein, the reaction being carried out under esterifying conditions with a sufficient amount of such fatty acids to provide complete esterification of both hydroxyl groups on the tertiary amine. Thereafter, the diesterified tertiary amine is reacted with a quaternizing reagent of the formula $CH_3X$, such as methylchloride or dimethylsulfate, in order to provide a second methyl group onto the nitrogen atom, thereby forming the desired quaternary ammonium compound.

The substituents $R^1$ and $R^2$ defined hereinabove are preferably both methyl, or both ethyl, or one is methyl or ethyl and the other is benzyl or hydroxyalkyl, preferably hydroxyethyl or hydroxymethyl.

In formula (1) as defined herein, the anion $X^-$ counterbalances the positive charge of the quaternary ammonium compound. Thus, the quaternizing compound has the formula $CH_3X$. The anion X is preferably any anion forming the desired compound capable of quaternizing the tertiary amines so as to form the desired dimethylsubstituted quaternary ammonium compound. Preferred examples of $X^-$ include chloride, bromide and methylsulfate.

Referring again to formula (1), the substituent R is selected from the group consisting of alkyl and alkylene groups containing 12 to 24 carbon atoms and 0, 1, 2 or 3 carbon-carbon double bonds. It has been determined that superior conditioning properties are exhibited by compounds corresponding to the above formula (1) provided that the compounds corresponding to that formula (1) which are present in the conditioning composition represent a mixture of chain lengths of the substituent R and also represent a mixture of saturated and mono-unsaturated and diunsaturated chains. It is recognized, of course, that any one compound of formula (1) can have no more than two particular R groups, and that within any one molecule the R groups can be the same or different. However, the superior conditioning properties that the conditioning compositions of the present invention have been found to possess are provided by including in the compositions compounds corresponding to formula (1) wherein compounds are present which exhibit R groups containing at least five different chain lengths and containing R groups which have no carbon-carbon double bonds, R groups which have one carbon-carbon double bond, and R groups which have two carbon-carbon double bonds. Hair and skin conditioning compositions containing mixtures of compounds of formula (1) have been found to exhibit conditioning superior to that exhibited by conditioning agents of formula (1) wherein all the R groups are the same.

The requirement that the conditioning compositions contain compounds of formula (1) exhibiting a number of different chain lengths and degrees of saturation can be readily met by reacting the precursor bis(hydroxyl) tertiary amine with products containing a mixture of fatty acids of varying chain lengths and varying degrees of unsaturation. Such mixtures of acids are known and are commercially available as, for instance, tallow acids, rapeseed oil acids, palm oil acids, palm stearine acids, and canola oil acids, which are particularly preferred examples as used in the present invention. The fatty acids present in each of these naturally occurring products contain five or more different chain lengths and contain acids having no unsaturation, as well as acids which are mono-unsaturated, di-unsaturated and tri-unsaturated. More particularly, the distribution of fatty acids and their chain lengths and number of double bonds are set forth in the following table.

The following table describes tallow acids and rapeseed oil acids, which are two preferred acid mixtures useful in this invention. Each number represents a percent by weight of the entire mixture of acids and has a margin of ±0.2 wt. %.

| Fatty Acids | Carbon Atoms | Double Bonds | Tallow | Rapeseed Oil |
|---|---|---|---|---|
| Lauric | 12 | 0 | 0.1 | — |
| Myristic | 14 | 0 | 3.2 | 0.1 |
| Myristoleic | 14 | 1 | 0.9 | — |
| Pentadecanoic | 15 | 0 | 0.5 | — |
| Palmitic | 16 | 0 | 24.3 | 3.8 |
| Palmitoleic | 16 | 1 | 3.7 | 0.3 |
| Margaric | 17 | 0 | 1.5 | — |
| Margaroleic | 17 | 1 | 0.8 | — |
| Stearic | 18 | 0 | 18.6 | 1.2 |
| Oleic | 18 | 1 | 42.6 | 18.5 |
| Linoleic | 18 | 2 | 2.6 | 14.5 |
| Linolenic | 18 | 3 | 0.7 | 11.0 |
| Arachidonic | 20 | 0 | 0.2 | 0.7 |
| Gadoleic | 20 | 1 | 0.3 | 6.6 |
| Eicosadienoic | 20 | 2 | — | 0.7 |
| Behenic | 22 | 0 | — | 0.5 |
| Erucic | 22 | 1 | — | 41.1 |
| Lignoceric | 24 | 0 | — | 1.0 |
| Iodine Value Range | | | 40–55 | 100–115 |

The compositions according to the present invention can be formulated with any cosmetically acceptable vehicle which is inert to the conditioning agent and to the hair or skin, as the case may be. By "cosmetically acceptable" is meant that the vehicle is inert to the skin or hair and permits easy, even application to the skin or hair of a thin film which contains the reaction product. Such vehicles can comprise any of a large variety of forms, including oil-in-water emulsions, water-in-oil emulsions, anhydrous compositions such as oil-based liquids, slurries, powders or pastes, and aqueous solutions, slurries and pastes. The conditioning compositions preferably contain a total of from about 0.1 wt. % to about 10 wt. % of the indicated mixture of compounds of the formula (1).

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl ricinoleate, glyceryl stearate, propane-1,2-diol, butane-1,3-diol, mink oil, cetyl alcohol, stearamidopropyl dimethylamine, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, dimethicone copolyols, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate;

Solvents such as ethyl alcohol, propylene glycol, water, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, propylene glycol, gelatin;

Powders can include components such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, cellulosics such as hydroxyethyl cellulose and sodium carboxymethyl cellulose, ethylene glycol monostearate, zinc or magnesium stearate, zinc oxide and magnesium oxide. These components may also be used as thickeners in fluid or semi-fluid compositions.

Examples of additional composition types are found in *Encyclopedia of Chemical Technology*, Vol. 7, Pages 146–150 and 155–160 (John Wiley & Sons, 1979), the disclosure of which is hereby incorporated herein by reference.

Examples of other conventional adjuncts, some of which can also function as vehicles, that may optionally be employed, include volatile and nonvolatile silicones; silicone polymers; preservatives, such as para-hydroxy benzoate esters; humectants, such as butane-1,3-diol, glycerol, sorbitol, polyethylene glycol; stabilizers, such as sodium chloride or ammonium chloride; buffer systems, such as lactic acid together with a base such as sodium hydroxide; oils and waxes, such as avocado oil, Evening Primrose oil, mineral oil, petrolatum, sunflower oil, beeswax, ozokerite wax, paraffin wax, lanolin, lanolin alcohol; emollients; thickeners; activity enhancers; colorants; whiteners; fragrances; and bactericides.

When the desired conditioning composition is a solution, one can simply stir together the desired amount of the mixture of compounds of formula (1) together with the solvent, such as water or, for instance, a lower alcohol containing 1–6 carbon atoms in which the mixture is soluble, or a mixture of water and such an alcoholic component. A useful embodiment is a solution of 85% active and 15% ethanol. A preferred embodiment is 75% active and 25% propylene glycol.

When it is desired that the composition is in the form of an emulsion, for instance as a cream or lotion, the composition should also contain an emulsifier component which is constituted of one or more emulsifiers chosen to provide the HLB (hydrophilic-lipophilic balance) appropriate to whether the aqueous or oil phase is the continuous phase, and appropriate to the choice of the particular components present. Suitable cosmetically acceptable emulsifiers abound and are well known to the cosmetic chemist. Examples include compounds having a long-chain alkyl or alkylene chain of 12 to 20 carbon atoms substituted with a chain of 4 to 20 ethoxy or propoxy units; and glycol or glycerol derivatives substituted with an alkyl or alkylene chain of 12 to 24 carbon atoms. Further examples are found in *Encyclopedia of Chemical Technology*, Vol. 8, Pages 913–916 (John Wiley & Sons, 1979), which are hereby incorporated herein by reference.

The topical skin conditioner compositions of the invention can be formulated as a fluid, for example in a product such as a lotion, with or without an applicator such as a roll-ball applicator, or a container fitted with a pump to dispense the composition, for example as a cream or mousse, or simply in a non-deformable bottle or squeeze container. Alternatively, the composition of the invention may be semi-solid, for example as a cream, lotion, gel, paste or ointment for use in conjunction with a suitable applicator or simply in a tube or lidded jar. Hair and skin conditioner compositions are preferably flowable liquids (solutions, emulsions or dispersions) although they can be in the form of thickened gels, pastes and the like that can be rubbed into and onto the hair or skin.

The conditioning compositions useful in the present invention will preferably contain in addition substances effective to adjust the pH of the composition to values within desired ranges compatible with the surface to which the conditioning agent will be applied. Thus, for instance, it is preferred that the pH of a hair conditioning composition be in the range of about 4.0 to about 5.5 in order to provide proper compatibility with the hair shaft itself. It is preferred that skin conditioning compositions have a pH of about 3.5 to about 5.5 in order to provide proper conditioning to the skin while avoiding irritation that would ensue from pH values that are too low or too high. Suitable agents for adjusting the pH to within these desired limits without otherwise disturbing the desired attributes of the conditioning compositions include citric acid (to adjust the pH downwards) and small amounts of sodium hydroxide (to adjust the pH upwards).

The conditioning compositions can also contain additional adjuvants which enhance the conditioning properties of the compositions and agents which provide fluidity to the composition. As is familiar to those having experience in this field, the conditioning compositions are preferably flowable liquids which retain sufficient viscosity that they do not immediately run off of the surface to which they are applied.

Thus, it is preferred that the conditioning compositions include one or more fatty alcohols, by which is meant compositions of the formula $R^1OH$ wherein $R^1$ represents an alkyl or alkylene group, straight or branched, containing 12–22 carbon atoms and 0, 1 or 2 carbon-carbon double bonds.

The formulation of the compositions is straightforward and well within the skill of those familiar with the manufacture of conditioning compositions. The ingredients are stirred together in a suitable mixing vessel until a homogeneous flowable composition is formed. The composition is then metered into appropriate containers, sealed and available for shipment to the point of purchase.

The resulting conditioning compositions can be used in the manner presently employed with conventional hair conditioning compositions and skin conditioning compositions. For use on the hair, it is adequate to pour an amount generally ranging from about 1 to about 5 grams onto the hair, to work it into the hair thoroughly, and then to rinse it from the hair. For skin conditioning compositions, amounts generally used are on the order of 0.5 to 2 fluid ounces which are applied to the skin or applied to the hands and then rubbed onto the skin with any excess amounts of conditioner simply wiped off of the skin. It will be recognized that the appropriate amount to use can readily be ascertained as a function of the conditioning effect imparted by the composition and as a function of the volume of hair or area of skin that is desired to be conditioned.

The present invention will be further illustrated in the following examples, which are included for purposes of illustration and are not intended to be limiting.

EXAMPLE 1

This example compares compositions in accordance with the present invention with other formulations for properties as a hair conditioner.

The formulations that were tested were:

| Ingredient | Wt. % |
| --- | --- |
| Formulation 1-1 | |
| Quaternium-18 (dimethyldihydrogenated tallow ammonium chloride), 68% active in propylene glycol ("Varisoft 432 PPG," Witco Chemical Co.) | 1.47 |
| Cetyl Alcohol ($CH_3(CH_2)_{15}OH$) | 2.0 |
| Ceteareth-20 (having the formula $R(OCH_2CH_2)_nOH$ wherein R is a mixture of cetyl and stearyl and n has an average value of 20) | 1.0 |
| Citric acid, as 25 wt. % solution in water | to pH 4.0–4.4 |
| DI (deionized) Water | 95.53 |
| Formulation 1-2 | |
| PPG-9 Dimethylmonium chloride (Methyl-diethyl-poly(propoxy)-ammonium chloride having an average of 9 propoxy units) 95% active in water ("Emcol CC-9," Witco Chemical Co.) | 1.05 |
| Cetyl Alcohol | 2.0 |
| Ceteareth-20 | 1.0 |
| Citric acid, as 25 wt. % solution in water | to pH 4.0–4.4 |
| DI Water | 95.95 |
| Formulation 1-3 | |
| PPG-40 Diethylmonium chloride Methyl-diethyl-poly(propoxy)-ammonium chloride having an average of 40 propoxy units) ("Emcol CC-42," Witco Chemical Co.) | 1.05 |
| Cetyl Alcohol | 2.0 |
| Ceteareth-20 | 1.0 |
| Citric acid, as 25 wt. % solution in water | to pH 4.0–4.4 |
| DI Water | 95.95 |
| Formulation 1-4 | |
| Steapyrium chloride (1-(2-hydroxyethyl) carbamoyl methyl pyridinium chloride stearate), 94% active ("Emcol E-607S," Witco Chemical Co.) | 1.06 |
| Cetyl Alcohol | 2.0 |
| Ceteareth-20 | 1.0 |
| DI Water | 95.94 |
| Citric acid, as 25 wt. % solution in water | to pH 4.0–4.4 |
| Formulation 1-5 | |
| Lapyrium chloride (1-(2-hydroxyethyl) carbamoyl methyl pyridinium chloride laurate), 97.5% active ("Emcol E-607L," Witco Chemical Co.) | 1.06 |
| Cetyl Alcohol | 2.0 |
| Ceteareth-20 | 1.0 |
| DI Water | 95.97 |
| Citric acid, as 25 wt. % solution in water | to pH 4.0–4.4 |
| Formulation 1-6 | |
| Mixture of compounds of formula (1), derived from soft (partially hydrogenated) tallow acids, 82% actives, X = Cl | 1.22 |
| Cetyl Alcohol | 2..0 |
| Ceteareth-20 | 1.0 |
| DI Water | 95.78 |
| Citric acid, as 25 wt. % solution in water | to pH 4.0–4.4 |
| Formulation 1-7 | |
| Mixture of compounds of formula (1), derived from hydrogenated tallow acids, 82% active, X = Cl | 1.22 |
| Cetyl Alcohol | 2.0 |
| Ceteareth-20 | 1.0 |
| DI Water | 95.78 |
| Citric acid, as 25 wt. % solution in water | to pH 4.0–4.4 |

Each formulation was prepared as follows: the water, and separately the ingredients other than water or citric acid, were measured into separate beakers. Each beaker was heated over a steam bath until the contents were at 75°–80° C. The beakers were then removed from the heat, the contents were combined and stirred until cool, and citric acid as necessary was added.

A hair swatch evaluation test was then performed to assess the performance of each formulation as a hair conditioner. Hair swatches were prepared and tested as follows:

Hair for the tests was certified virgin European brown hair. The hair samples were banded and glued in 5 gram tresses.

Procedure:
1. Wet hair tress with warm tap water and apply 3 cc of a 5 wt. % solution of sodium lauryl sulfate in deionized water.
2. Wash hair for 2 minutes and rinse for 1 minute under running tap water at 40° C.
3. Squeeze excess water from hair and place tress in large weighing dish.
4. Weigh 0.5 gram of a 1% active conditioner onto the hair tress.
5. Massage conditioner evenly through the hair for 2 minutes and rinse for 1 minute under running tap water at 40° C.
6. Squeeze out excess water and blot dry between layers of paper towels.
7. Comb hair and evaluate for wet comb and wet detangle.
8. Roll hair onto a 1-inch plastic roller and hang to dry overnight.
9. Remove roller and evaluate for dry characteristics including dry comb, manageability, dry detangle, bounce/body, curl, and shine.
10. Report results as a number (5=best) and/or use descriptive words.

These results indicate that hair conditioning compositions in accordance with the present invention exhibit superior conditioning.

The results are set forth in the following Table 1:

TABLE 1

| Conditioner Formulation | 1-1 | 1-2 | 1-3 | 1-4 | 1-5 | 1-6 | 1-7 |
|---|---|---|---|---|---|---|---|
| Feel on Hair | 3.0 | 3.0 | 2.5 | 4.0 | 4.5 | 5.0 | 5.0 |
| Rinsability | 3.5 | 3.0 | 3.5 | 4.0 | 4.5 | 4.5 | 4.5 |
| Wet Comb | 3.5 | 3.0 | 3.0 | 4.0 | 4.5 | 4.5 | 4.5 |
| Detangle | 3.0 | 3.0 | 2.5 | 3.5 | 4.5 | 4.5 | 4.0 |
| Dry Comb | 3.0 | 3.0 | 2.5 | 4.0 | 3.5 | 4.0 | 4.0 |
| Detangle | 3.5 | 2.5 | 2.0 | 4.5 | 3.5 | 4.0 | 3.5 |
| Antistatic | 2.5 | 2.5 | 2.0 | 3.5 | 3.0 | 3.5 | 3.5 |
| Bounce/Body | 3.5 | 3.0 | 2.5 | 3.0 | 3.0 | 3.5 | 3.5 |
| Manageability | 3.0 | 3.0 | 2.5 | 3.5 | 3.0 | 3.5 | 3.5 |
| Shine | 3.0 | 3.0 | 2.0 | 3.0 | 3.0 | 3.0 | 3.0 |
| Total (Average) | 3.15 | 2.9 | 2.5 | 3.7 | 3.7 | 4.0 | 3.9 |

These results indicate that hair conditioning compositions in accordance with the present invention exhibit superior conditioning compound to compositions based on other conditioning agents.

EXAMPLE 2

This example compares compositions in accordance with the present invention with compositions based on agents of a single chain length R.

The formulations that were tested were:

| Ingredient | Wt. % |
|---|---|
| Formulation 2-1 | |
| A compound corresponding to formula (1) except that both R groups were $C_{13}$ alkyl, X = Cl | 1.0 |
| Cetyl Alcohol | 2.0 |
| Ceteareth-20 | 1.0 |
| DI Water | 96.0 |
| Citric acid, as 25 wt. % solution in water | to pH 4.0–4.4 |
| Formulation 2-2 | |
| A compound corresponding to formula (1) except that both R groups were $C_{15}$ alkyl, X = Cl | 1.0 |
| Cetyl Alcohol | 2.0 |
| Ceteareth-20 | 1.0 |
| DI Water | 96.0 |
| Citric acid, as 25 wt. % solution in water | to pH 4.0–4.4 |
| Formulation 2-3 | |
| A compound corresponding to formula (1) except that both R groups were $C_{17}$ alkyl, X = Cl | 1.0 |
| Cetyl Alcohol | 2.0 |
| Ceteareth-20 | 1.0 |
| DI Water | 96.0 |
| Citric acid, as 25 wt. % solution in water | to pH 4.0–4.4 |
| Formulation 2-4 | |
| Conditioning agent of formula (1) derived from hydrogenated tallow acids, X = $CH_3SO_4$ | 1.0 |
| Cetyl Alcohol | 2.0 |
| Ceteareth-20 | 1.0 |
| DI Water | 96.0 |
| Citric acid, as 25 wt. % solution in water | to pH 4.0–4.4 |
| Formulation 2-5 | |
| Conditioning agent as in Formulation 2-4 except that all R groups were $C_{13}$ alkyl | 1.0 |
| Cetyl Alcohol | 2.0 |
| Ceteareth-20 | 1.0 |
| DI Water | 96.0 |
| Citric acid, as 25 wt. % solution in water | to pH 4.0–4.4 |
| Formulation 2-6 | |
| Conditioning agent of formula (1) derived from rapeseed oil acids, X = Cl, (71.3% actives) | 1.15 |
| Cetyl Alcohol | 2.0 |
| Ceteareth-20 | 1.0 |
| DI Water | 95.85 |
| Citric acid, as 25 wt. % solution in water | to pH 4.0–4.4 |

Each formulation was prepared by combining the first listed product and the water in one container, combining the other ingredients in a separate container, heating each container over a steam bath until the contents were at 75°–80° C., removing the heat, combining the contents of the two containers, and stirring the product until cool.

Each formulation was then tested on hair following the procedure described in Example 1. The results are set forth in Table 2:

TABLE 2

| Conditioner Formulation | 1-1 | 1-6 | 1-7 | 2-1 | 2-2 | 2-3 | 2-4 | 2-5 | 2-6 |
|---|---|---|---|---|---|---|---|---|---|
| Feel on Hair | 3.0 | 5.0 | 5.0 | 2.7 | 4.9 | 4.9 | 4.9 | 2.6 | 5.0 |
| Rinsability | 3.5 | 4.5 | 4.5 | 3.5 | 4.5 | 4.5 | 4.5 | 3.3 | 4.5 |
| Wet Comb | 3.2 | 4.5 | 4.5 | 2.9 | 4.6 | 4.5 | 4.5 | 2.5 | 4.6 |
| Detangle | 3.0 | 4.6 | 4.4 | 2.3 | 4.0 | 4.2 | 4.5 | 2.1 | 4.6 |
| Dry Comb | 3.3 | 4.0 | 4.0 | 2.7 | 4.0 | 4.0 | 3.9 | 2.0 | 4.2 |
| Detangle | 3.5 | 4.0 | 3.7 | 3.0 | 4.5 | 4.5 | 4.0 | 2.5 | 4.3 |
| Antistatic | 2.5 | 3.5 | 3.5 | 2.3 | 3.0 | 3.5 | 3.0 | 2.3 | 3.0 |
| Bounce/Body | 3.5 | 3.5 | 3.5 | 3.0 | 3.5 | 3.5 | 3.2 | 2.9 | 3.2 |
| Manageability | 3.0 | 3.5 | 3.5 | 3.0 | 3.5 | 3.5 | 3.2 | 2.9 | 3.2 |
| Shine | 3.0 | 3.0 | 3.0 | 3.0 | 3.0 | 3.0 | 3.0 | 3.0 | 3.0 |
| Total (Average) | 3.15 | 4.01 | 3.96 | 2.84 | 3.95 | 4.01 | 2.86 | 2.61 | 3.96 |

These data show that conditioning agents based on a combination of compounds having a range of R chain lengths have superior performance even though they include compounds which used singly exhibit poorer conditioning and would thus be expected to detract from the performance of the combination.

EXAMPLE 3

This example describes the preparation of conditioner compositions of this invention.

| Formulation 3-1: Hair Conditioner | |
|---|---|
| Ingredient | Wt. % |
| Glyceryl Stearate | 1.0 |
| Cetyl Alcohol | 1.5 |
| Conditioning agent of formula (1) derived from rapeseed oil acids, X = Cl (71.3% actives) | 1.4 |
| DI Water | 95.0 |
| Hydroxyethylcellulose "Natrosol 250 HHR CS" (Aqualon) | 1.0 |
| Dimethicone Copolyol - Dow Corning 193 | 0.1 |
| Citric Acid (25% aqueous) | to pH 4.5–5.5 |
| Perfume | q.s |
| Preservative | q.s |
| | 100% |

Procedure:

Weigh water into a container. Sprinkle in Natrosol with mixing until there is an even distribution. Weigh glyceryl stearate, cetyl alcohol, and rapeseed conditioning agent into a separate container. Heat the contents of each beaker over a steam bath to 70°–75° C. Remove water cellulose mixture from bath, attach to agitator, then add in the contents of the other container to the water with mixing. The combination temperature was recorded at 700° C. Allow to cool. At 50° C. add premeasured dimethicone copolyol. After 24 hours the pH was adjusted with 25% citric acid.

Viscosity:

Brookfield Viscometer DV2

Spindle No. 5 at 10 rpm.

8,000 cps.

The product was a creamy, thick, white liquid at room temperature and retained this condition, without breaking, upon heating to 48° C. and after 3 freeze/thaw cycles. As a hair conditioner it provides excellent feel and detangling benefits.

| Formulation 3-2: Hair Conditioner | |
|---|---|
| Ingredient | Wt. % |
| DI Water | 90.7 |
| Cetyl Alcohol | 3.0 |
| Stearyl Alcohol | 0.5 |
| Conditioning agent of formula (1) derived from rapeseed oil acids, X = Cl (71.3% actives) | 2.8 |
| Ceteareth-20 | 0.4 |
| Stearamidopropyl Dimethylamine | 0.3 |
| DI Water | 2.0 |
| Hydrolyzed Protein - "Crotein SPC" (Croda) | 0.3 |
| Citric Acid (25% aqueous) | to pH 4.5–5.5 |
| Perfume | q.s |
| Preservative | q.s |
| | 100% |

Observations & Data:

The water was weighed into a container. The other ingredients other than water and citric acid were weighed into a separate container. The contents of each container were heated over a steam bath to 70°–75° C. The water was removed from the steam bath and attached to a mixer, and the second container contents were added with agitation. The mixture was allowed to cool with mixing. At 30° C. premixed water and hydrolyzed protein were added. After set-up the pH was adjusted with citric acid.

Viscosity:

Brookfield DV2 Viscometer.

Spindle No. 5 at 10 rpm.

2,520 cps.

The product was a thin, creamy, white liquid and retained this condition, without breaking, upon heating at 48° C. and after 3 freeze/thaw cycles. It is a deep conditioning hair conditioner with exceptional afterfeel.

| Formulation 3-3: Skin Lotion | |
|---|---|
| | Amt. (gr.) |
| Glyceryl Stearate | 4.0 |
| "Protol" (Mineral Oil) (Witco Corp.) | 2.0 |
| Cetyl Alcohol | 1.0 |
| PEG-8 Stearate | 1.0 |
| Conditioning agent of formula (1) derived from rapeseed oil acids, X = Cl, 71.3% actives | 1.3 |

-continued

Formulation 3-3: Skin Lotion

| | Amt. (gr.) |
|---|---|
| Dow Corning fluid 200 250 CS (Dow Chemical) | 0.4 |
| DI Water | 86.3 |
| Glycerine | 4.0 |
| Lactic Acid | pH 4.5–5.0 |
| pH = 3.9 | |

Viscosity:

Brookfield DV2 Viscometer.

Spindle No. 4 at 20 rpm.

78,000 cps.

The product appeared to be a water-in-oil emulsion and imparted a silky feeling to the skin.

Formulation 3-4: Skin Lotion

| | Amt. (gr.) |
|---|---|
| PPG-3 Myristyl ether | 6.0 |
| Glyceryl stearate | 3.5 |
| Conditioning agent of formula (1) derived from rapeseed oil acids, X = Cl | 1.3 |
| PEG-8 Stearate | 1.0 |
| Cetyl Alcohol | 0.5 |
| Petrolatum | 1.0 |
| Glycerine | 4.0 |
| Lactic Acid | 0.05 |
| DI Water | 82.65 |

Viscosity:

Brookfield DV2 Viscometer.

Spindle No. 4 at 20 rpm.

3,200 cps.

This product is an oil-in-water emulsion with good after-dry feel.

What is claimed is:

1. A method for conditioning hair comprising applying to the hair a conditioning effective amount of a composition comprising (a) from 0.1 wt. % to 10 wt. % of a mixture of compounds of the formula (1)

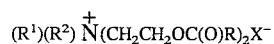 (1)

wherein $R^1$ is alkyl containing 1 to 6 carbon atoms, or hydroxyalkyl containing 1 to 6 carbon atoms; $R^2$ is alkyl containing 1 to 6 carbon atoms, or benzyl; $X^-$ is an anion; and R is selected from the group consisting of alkyl and alkylene groups containing 11 to 23 carbon atoms and up to 3 carbon-carbon double bonds, provided that said mixture contains compounds of formula (1) containing R groups which have at least 2 different chain lengths and containing R groups which have 0, 1 and 2 carbon-carbon double bonds; and (b) a cosmetically acceptable vehicle which imparts to said composition fluidity upon application thereof to the hair and which has a pH value compatible with said hair.

2. A method according to claim 1 wherein the pH value of said composition is about 3.5 to about 5.5.

3. A method according to claim 1 wherein said composition is a solution.

4. A method according to claim 1 wherein said composition is a water-in-oil emulsion.

5. A method according to claim 1 wherein said composition is an oil-in-water emulsion.

6. A method according to claim 1 wherein the structures of the R groups and the amounts thereof are those of tallow.

7. A method according to claim 1 wherein the structures of the R groups and the amounts thereof are those of palm stearine.

8. A method according to claim 1 wherein the structures of the R groups and the amounts thereof are those of palm oil.

9. A method according to claim 1 wherein the structures of the R groups and the amounts thereof are those of canola oil.

10. A method according to claim 1 wherein the structures of the R groups and the amounts thereof are those of rapeseed oil.

11. A method according to claim 1 wherein $X^-$ is selected from the group consisting of chloride, bromide, methylsulfate and ethylsulfate.

12. A method according to claim 1 wherein $R^1$ and $R^2$ are the same or different and are $C_1$–$C_2$ alkyl.

13. A method according to claim 12 wherein $R^1$ and $R^2$ are methyl.

14. A method according to claim 1 wherein $R^1$ is methyl or ethyl and $R^2$ is benzyl or hydroxyalkyl.

* * * * *